United States Patent [19]

Naicker et al.

[11] Patent Number: 4,935,503

[45] Date of Patent: Jun. 19, 1990

[54] AZIDOCHLORINATION AND DIAZIDIZATION OF GLYCALS

[75] Inventors: Selvaraj Naicker, Edmonton; Anthony A. Noujaim, Sherwood Park, both of Canada

[73] Assignee: Biomira, Inc., Edmonton, Alberta, Canada

[21] Appl. No.: 190,439

[22] Filed: May 5, 1988

[51] Int. Cl.$^5$ ............................................. C07H 11/02
[52] U.S. Cl. .................................. 536/17.2; 536/18.7; 536/122; 536/124; 562/433
[58] Field of Search ..................... 536/4.1, 17.2, 17.3, 536/17.7, 18.7, 53, 122, 123, 124; 562/433

[56] References Cited

U.S. PATENT DOCUMENTS

| | | | |
|---|---|---|---|
| 4,195,174 | 3/1980 | Lemieux et al. | 536/18 |
| 4,308,376 | 12/1981 | Lemieux et al. | 536/18 |
| 4,362,720 | 12/1982 | Lemieux et al. | 514/25 |

OTHER PUBLICATIONS

Bovin et al., Carbohydrate Res., 98:25–35 (1981).
Galli et al., Org. Prep. and Proceed., Int. 3(5):227–230 (1971).
Lemieux, Can. J. Chem., 57:1124 (1979).
Chem. Ab. 49:7248g, 55:21944.
Dahnmen et al., Carbohydrate Research, 111:C1–C4 (1982).
Kunz et al., Angew. Chem. Int. Ed. Engl. 25(4):360 (1986).
Lemieux et al., J. Am Chem. Soc., 97(14) (1975).
Paulsen et al., Carbohydrate Res., 104:195 (1982).

*Primary Examiner*—Johnnie R. Brown
*Assistant Examiner*—Elli Peselev
*Attorney, Agent, or Firm*—Iver P. Cooper

[57] ABSTRACT

The invention describes a one-pot single step procedure for the azidochlorination or diazidization of glycals, including glycal elements of carbohydrates. Compounds such as 3,4,6-tri-O-benzyl-2-azido-2-deoxy-alpha-D-galactopyranosy chloride, and 3,4,6-tri-O-benzyl-2-azido-2-deoxy-alpha-,beta-D-galactopyranose are prepared from tri-O-benzyl galactal as well as 3,4,6-tri-O-acetyl-2-azido-2-deoxy-D-alpha-galactopyranasol chloride and 3,6-di-O-acetyl-4-O-[2,3,4,6-tetra-O-acetyl-beta-D-galactopyranosyl]-2-azido-2-deoxy-alpha-D-glycopyranosyl chloride from their respective O-acetylated glycal derivatives by the addition of azido chloride which is chemically generated in situ. A method using 3,4,6-tri-O-acetyl-2-azido-2-deoxy-alpha-D-galactopyranosyl chloride for the synthesis of antigenic determinants such as the terminal asialo $GM_1$(beta-D-Gal (1->3)-beta-D-GalNAc-OR) has been demonstrated. The conversion of the subject synthon into 3,4,6-tri-O-acetyl-2-azido-2-deoxy-alpha-D-galactopyranosyl bromide and 1,3,4,6-tetra-O-acetyl-2-azido-2-deoxy-alpha-D-galactopyranose is also described. A further method for the synthetic generation of the Tn antigen (alpha-D-GalNAc-O-L-serine) is also described.

31 Claims, 5 Drawing Sheets

AZIDOCHLORINATION OF LACTAL

FIG. 5.

SYNTHESIS OF Tn-α-O-SERINE a) (COBr)$_2$, DMF
b) Et$_4$N$^+$Br$^-$, DMF
c) NaBH$_4$, NiCl$_2$
d) H$_2$-Pd/C

AZIDOCHLORINATION AND DIAZIDIZATION OF GLYCALS

BACKGROUND OF THE INVENTION

1. Field of the Invention

This invention relates to a novel procedure for the azidochlorination or diazidization of glycals.

2. Information Disclosure Statement

Numerous antigens of clinical significance bear carbohydrate determinants. The blood group precursor Thomsen-Friedenreich (TF) and Tn-antigens are considered to be carcinoma markers. These antigens are synthesized intracellularly and then covered by covalently-linked carbohydrates. Both are found in the unmasked immunoreactive form on the external surface membranes of most primary carcinomas and their metastases (>90% of human carcinomas). As cancer markers, TF and Tn permit early immunohistochemical detection and prognostication of the invasiveness of some carcinoma. It has been shown by Springer, et al., that these antigens are not found in sarcomas, malignant tumors of the CNS, benign tumors, and tissues with non-carcinomas disease (Springer, et al., Naturewissen—schajten, 61, 457–458, 1974).

There is thus considerable interest in preparing these and other carbohydrate determinants synthetically for use as haptens. Joined to suitable carriers, these molecules become synthetic immunogens, as well.

It is known that glycals, and more particularly galactals, may participate in addition reactions with suitable reagents, such as $IN_3$, $ClN_3$, $ICl$, $(SCN)_2$ and Cl—N—H—O—C(O)R. See Brimacombe, et al., Chem. Comm. 1401 (1968); Igarashi, et al., J. Org. Chem. 32: 2521–30 (1967); Lessard, et al., Tetrahedron Lett., 56: 4887–90 (1970); Bovin, et al., Carbohydr. Res., 98: 25–35 (1981). The reagent adds at carbons 1 and 2. (The carbons at positions 3, 5 and 6 are protected, usually by benzyl or acetyl groups.) Bovin, et al. (1981), while reporting the addition of azidochloride to 3,4,6,-tri-O-acetyl-D-galactal and to 3,4,6-tri-O-benzyl-D-galactal under photolytic conditions, were unable to actually isolate the azidochloride derivative. However, they converted the crude product first into an azido-acetate derivative and then into an azido-bromide derivative, both of which were isolated.

Known techniques of preparing the desired 2-azido glycosyl chlorides are unsatisfactory. Paulsen, et al., Chem. Ber. III: 2358–69 (1978) described a ten-step procedure for the synthesis of 6-O-acetyl-2-azido-3,4-di-O-benzyl-2-deoxy-beta-D-galactopryanosyl chloride. This complicated approach did not win favor.

Lemieux, et al. Can. J. Chem. 57: 1244–51 (1979) and U.S. Pat. Nos. 4,308,376; 4,362,720 and 4,195,174 recommended a two step procedure in which an O-protected glycal was azidonitrated and the azidonitrate group was subsequently displaced by chloride (from tetraethylammonium chloride). At both stages, column chromatography was necessary to isolate the desired compound. In the method reported by Lemieux, et al., azidonitration of tri-O-acetylgalactal provided 53% of 3,4,6-tri-O-acetyl-2-azido-2-deoxy-beta-D-galactopyranosylol nitrate, 22% of 3,4,6-tri-O-acetyl-2-azido-2-deoxy-alpha-D-galactopyranosyl nitrate, 8% of the talo isomer and 5% of N-acetyl-3,4,6-tri-O-acetyl-2-azido-2-deoxy-alpha-O-galactopyranosylamine. In addition to these products, the hydrolyzed product will also be formed. The last two derivatives are the undesirable by-products which need to be separated. Thus, the azidonitration approach necessitates extensive separation of the products by liquid chromatography.

Bovin, et al., Carbohydr. Res. 98: 25–35 (1981) taught the addition of azidochloride to 3,4,6-tri-O-acetyl-D-galactal under UV irradiation. Azidochloride is highly explosive. See Chemical Abstract, 49: 7248g; Id., 55: 21944i. Lemieux, Can. J. Chem., 57: 1244, 1245 (1979) considered use of this reagent to induce free radical addition, but abandoned this approach "when a reaction involving chloroazide and with sulfuryl chloride as the radical initiator detonated with violence." Moreover, the use of UV irradiation meant that the chemist had to employ expensive quartz vessels (which transmit UV) and provide UV equipment. (Absent UV light, the reaction was greatly prolonged.)

Galli, et al., Org. Prep. and Proceed, Int., 3(5): 227–30 (1971) reported that alpha-chloro-beta-azidoethylbenzene could be prepared from styrene by reaction with $FeCl_3 \cdot 6H_2O$, $NaN_3$, $FeSO_4 \cdot 7H_2O$, and $(NH_4)_2S_2O_8$ (ammonium peroxydisulphate). Galli's procedure has not been used to azidochlorinate vinylic ethers such as O-protected-D-glycals.

SUMMARY OF THE INVENTION

Numerous glycoproteins containing units derived from 2-acetamido-2-deoxyhexoses, particularly 2-acetamido-2-deoxyalpha-D-galactopyranose, are known in nature. These units may be prepared from their 2-azido analogues by reduction of azido function. See Patai, THE CHEMISTRY OF THE AZIDO GROUP 332–338 (1971). Moreover, halide derivatives of these 2-azido sugars are useful as glycosylating agents in Koenigs-Knorr type reactions since the 2-azido substituent is nonparticipating, i.e., it does not affect the selection of an alpha or a beta glycosidic linkage. See Paulsen, et al., Angew. Chem. Int. Ed., 14: 558 (1978); Id., Tetrahedron Lett. 2301 (1976); Id., Angew. Chem. Int. Id. (Eng) 21: 155 (1982).

We have discovered a safe, simple ("one pot") and economical (purification by one stage of simple column chromatography and crystallization) method of preparing 3,4,6-protected, 2-azido-2-deoxyhexosyl chlorides and derivatives thereof. In particular, our method is useful for the preparation of:

(a) 3,4,6-tri-O-acetyl-2-azido-2-deoxy-alpha-D-galactopyranosyl chloride;

(b) 3,4,6-tri-O-benzyl-2-azido-2-deoxy-alpha-D-galactopyranosyl chloride;

(c) 3,4,6-tri-O-benzyl-2-azido-2-deoxy-alpha,beta-D-galactopyranose; and

(d) 3,6-di-O-acetyl-4-O-[2,3,4,6-tetra-O-acetyl-beta-D-galactopyranosyl]-2-azido-2-deoxy-alpha-D-glucopyranosyl chloride;

by the addition of in situ-generated azide radical and chloride ion to a suitable glycal. These synthons are useful in the preparation of antigenic determinants such as asialo-GM$_1$ (beta-D-Gal-(1->3)-beta-D-GalNAc-OR) and Tn (alpha-D-GalNAc-O-L-serine).

In our approach, a 3,4,6-O-acetyl (or -O-benzyl) 2-deoxyhexose is reacted with FeCl$_3$, NaN$_3$, FeSO$_4$ and (NH$_4$)$_2$S$_2$O$_8$.

The ferrous salt is oxidized by the ammonium peroxydisulfate to the ferric state, while a sulfate ion free radical is released. This free radical in turn reacts with the azide ion to generate an azide free radical. This reacts with the C-2 carbon of the sugar. A chloride ion then attacks the C-1 carbon, completing the azidochlorination.

We surmise that the reaction comprises the following steps:

However, the invention is not limited to any particular theory of mechanism.

With modification, the diazide derivative may be generated instead of the azidochloride. For example, by omitting ferric chloride, one may synthesize 3,4,6-tri-O-benzyl-1,2-diazido-1,2-deoxy-alpha-D-galactopyranose.

The technique may be used to prepare azidochlorides or diazides of monosaccharides, disaccharides, trisaccharides, and higher oligosaccharides. These azidochloride derivatives may be subsequently converted into the corresponding azidobromides, or conjugated with other glycosyl acceptors.

DETAILED DESCRIPTION OF THE INVENTION

This invention relates primarily to the azidochlorination or diazidation of glycals-containing carbohydrates. For the purpose of the appended claims, a "glycal" is a 1,2-unsaturated glycose, which may be substituted or unsubstituted at the other carbon positions. The term "carbohydrate" includes monosaccharides, disaccharides, trisaccharides, higher oligosaccharides, and polysaccharides. The carbohydrate may be merely a glycal, and the "glycal element" is then the carbohydrate itself. Or one or more elements of the carbohydrate may be glycals. The sugar units of the carbohydrate may be substituted with protective groups or glycosidically linked with an "aglycon" moiety.

Preferably, the glycal is a hexose, and most preferably it is a derivative of a galactose (a "galactal"). A manno configuration is not acceptable. 2-deoxy glucoses may be azidochlorinated, but the yield may be lower since the —OH at C-4 points downward. Other glycals, however, are believed to be suitable for azidochlorination or diazidation by the methods set forth herein. Fucals (6-deoxyglycals) are acceptable substrates, and so would be 4-deoxy or 3-deoxyglycals.

For purposes of subsequent glycosylation, the glycal will normally be protected at C-3, C-4 and/or C-6. Usually acetyl or benzyl protecting groups are preferred, the former being especially preferred. However, a combination of benzyl and acetyl groups, or the use of methyl or p-methoxybenzyl groups, among others, may be envisioned.

The acetyl groups are electron-withdrawing groups and decrease the reactivity of the glycal. If FeCl$_3$ is used for the redox oxidation system, the azidochloride derivative is formed. If Fe$_2$(SO$_4$)$_3$ is used, a diazide is obtained. If benzyl (an electron-releasing group) is used to protect the glycal, the outcome is different. The use of FeCl$_3$ then results in production of both azidochloride and diazide derivatives. Again, use of FeSO$_4$ alone results in production of the diazide.

Direct bromination is impractical because of the lower reactivity of the bromide; diazide is formed. However, the azidobromide may be prepared by hydrolysis of the azidochloride, following by treatment of the azidohydroxide with oxalylbromide in dimethylformamide (DMF).

While ferrous sulfate is the preferred oxidizable material because it is readily ionized, other ferrous salts, such as ferrous ammonium sulfate, ferrous chloride, ferrous carbonate and ferrous oxalate may be substituted. The hydrated ferrous sulfate is preferred over its anhydrous form.

The ammonium peroxydisulfate is an oxidizing agent and sulfate ion free radical source (by electron transfer from the ferrous ion). Other peroxydisulfate salts may be used, but the solvent system must be matched to their solubility characteristics.

Hydrogen peroxide is used to initiate the generation of sulfate free radical. Other initiators may be used, such as t-butylhydroperoxide and SO$_2$Cl$_2$. However, H$_2$O$_2$ is preferred because of the reduced risk of explosion.

The sodium azide is useful solely as a source of azide ion, and other azide salts such as ammonium or potassium azide, may replace it.

The ferric chloride reacts with the sodium azide to generate (FeN$_3$)$^{2+}$. The free chloride ion eventually attacks the C-1 carbon of the glycal.

Lithium chloride is a supplemental source of chloride ion, and it is desirable only when the glycal is protected with benzyl or similar groups.

An excess (2:1) of ammonium peroxydisulfate and of ferric chloride (4:1) relative to the sodium azide are used to drive the production of the azide free radical to completion. Other proportions may be used, but with lower yields.

Figure 4:
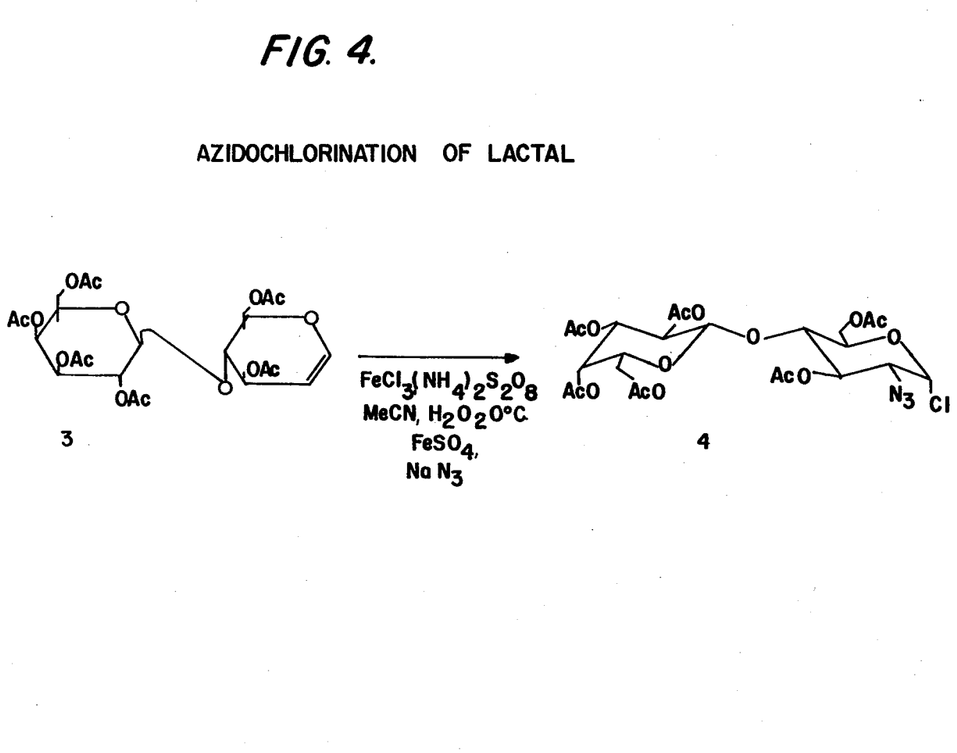
FIG. 4 shows the azidochlorination of a lactal (3).
Figure 5:
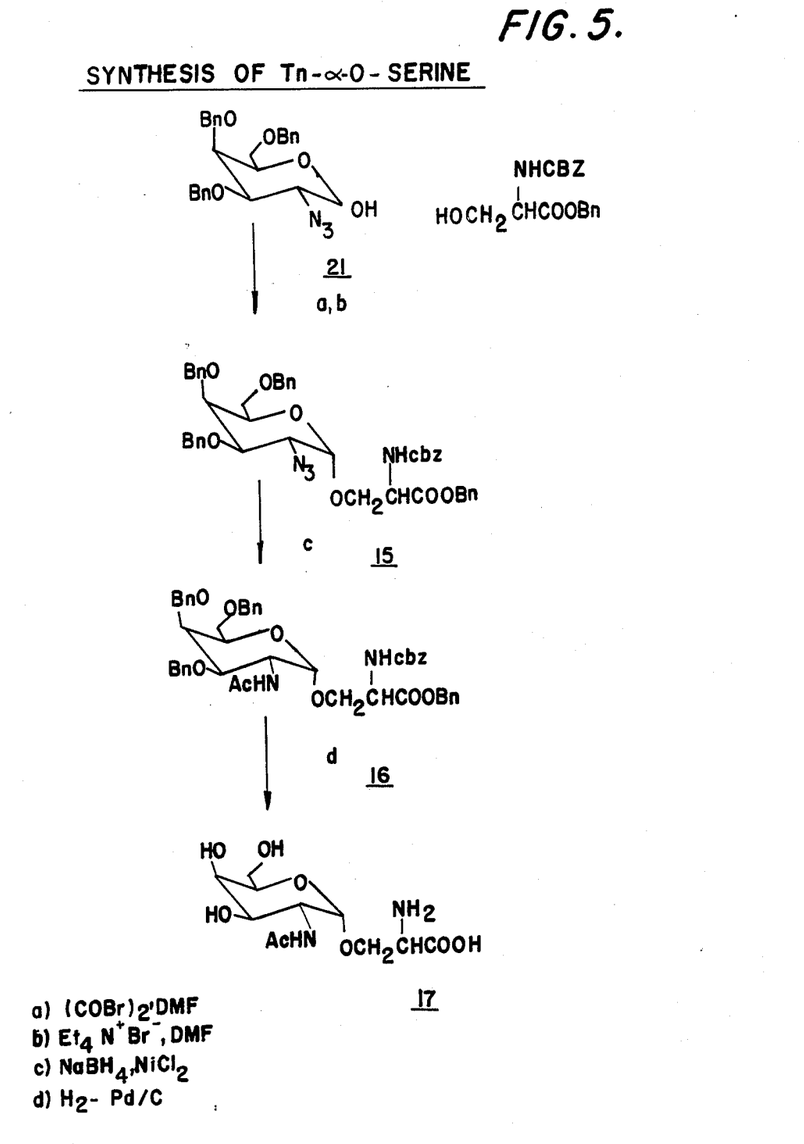
FIG. 5 depicts the synthesis of Tn-alpha-O-serine (17) from one of the products shown in FIG. 2.

The same method was used, starting from lactal, in the synthesis of 3,6-di-O-acetyl-4-O-[2,3,4,6-tetra-O-acetyl-beta-D-galactopyranosyl]-2-azido-2 -deoxy-alpha-D-glucopyranosyl chloride (4) an important reagent for the preparation of a variety of tumor and blood group antigens.

Figure 1:
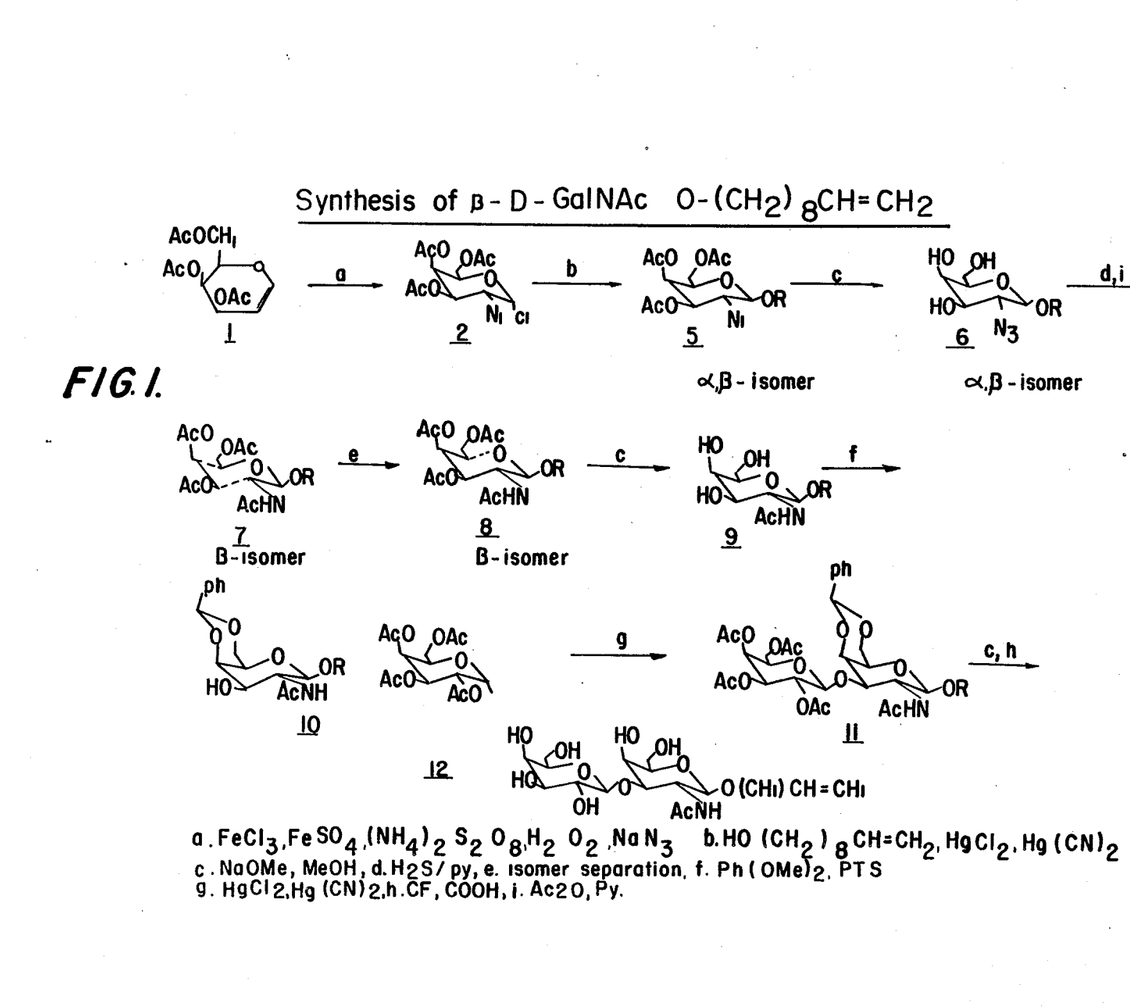
FIG. 1 depicts the total synthesis of beta-D-Gal (1-3-beta-D-GalNAc-O-$(CH_2)_8$CH=$CH_2$ (12), a synthetic asialo-GM1 hapten with an olefinic aglycon for use in linking the hapten to an immunological carrier. The first step is the azidochlorination of a -O-acetyl-protected galactal (1).
Figure 2:
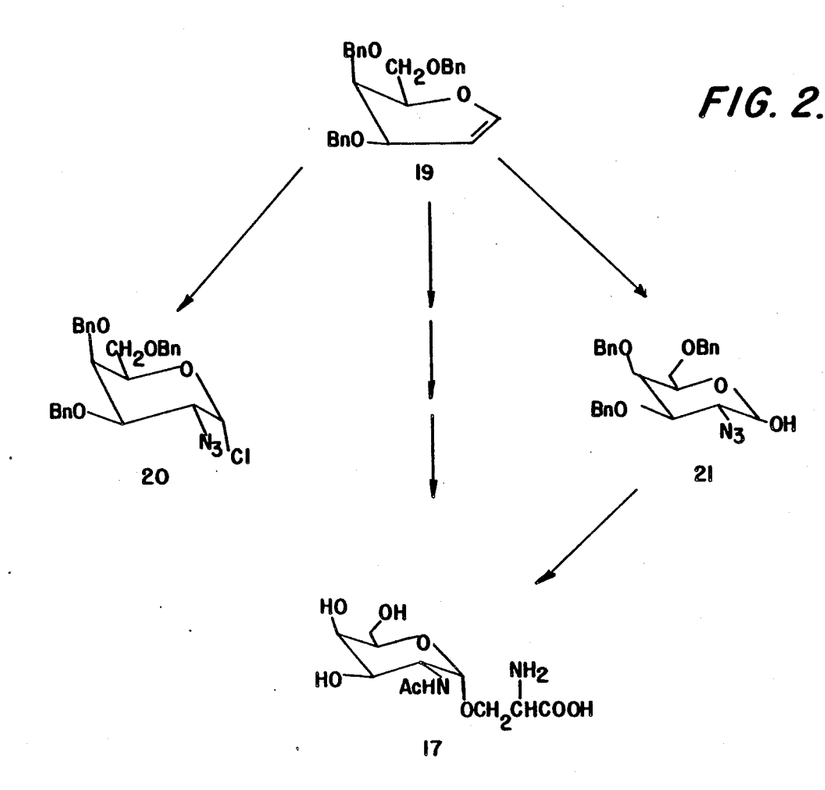
FIG. 2 shows azidochlorination of -O-benzyl-protected galactal (19).
Figure 3:
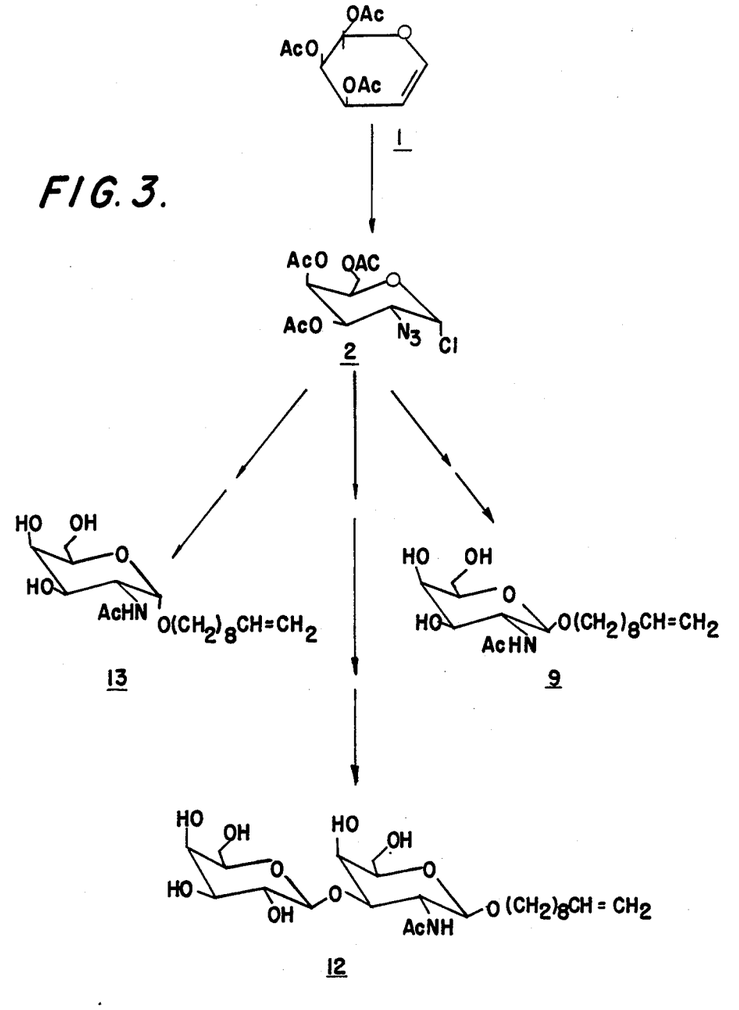
FIG. 3 shows preparation of other compounds of interest from the azidochloride (2) of FIG. 1.

The synthon 3,4,6-tri-O-acetyl-2-azido-2-deoxy-alpha-D-galactopyranosyl chloride (2) can be used to prepare alpha and beta glycosides as illustrated by the preparation of 9-decenyl-2-acetamido-2-deoxy-alpha-D-galactopyranoside (13) and 9-decenyl-2-acetamido-2-deoxy-beta-D-galactopyranoside (9). This azido chloride compound can also be converted into its acetate derivative (14) which further can be used to prepare alpha-glycosides by using trimethylsilyl triflate and pyridine mixture as reported by Shinkiti Koto, et al., Bull. Chem. Soc. Jpn. 59: 411-414 (1986).

Finally, 3,4,6-tri-O-acetyl-2-azido-2-deoxy-alpha-D-galactopyranosyl chloride (2) can be used to prepare synthetic antigenic determinants like asialo GM$_1$ (beta-D-Gal (1->3) beta-D-GalNAc-OR), Thomsen-Friedenreich antigen (TF) (beta-D-Gal(1->3)-alpha-D-GalNAc-OR), Tn (alpha-D-GalNAc-O-L-serine) and Forssman (alpha-D-GalNAc(1->3)-beta-D-GalNAc-OR), as demonstrated by reported methods (Paulsen, Angew. Chem. Int. ed. Engl. 21: 155-224 (1982); Carbohydr. Res. 100 143-167 (1982); Carbohydr. Res. 135: 71-84 (1984); Lemieux, et al., CA Patent No. 1,083,566).

This invention, in part, also relates to the synthesis of 9-decenyl-2-acetamido-2-deoxy-3-O-(beta-D-galactopyranosyl)-beta-D-galactopyranoside (12) as an illustrative example for the utility of the synthon 3,4,6-tri-O-acetyl-2-azido-2-deoxy-alpha-D-galactopyranosyl chloride. The disaccharide beta-D-Gal(1->3) beta-D-GalNAc constitutes one of the core structures of the O-glucosidically linked carbohydrate chains in many glycoproteins. It happens to be the terminal disaccharide of asialo-GM$_1$ and also a very important tumor associated marker. In view of these facts we have attempted to design the synthetic form of these tumor-associated antigens for the purpose of generating monoclonal antibodies for cancer diagnosis and therapy. The principle for constructing artificial carbohydrate containing antigens is based on the covalent attachment of the oligosaccharide to a macromolecular carrier (usually a protein) to closely emulate the natural carbohydrate architecture on the surface of the cancer cells. It is possible to attach the sugar molecules to the protein with a spacer arm as the aglycon between the carbohydrate and protein molecule. A number of spacer arms have been used with a length ranging from 3-8 carbon chains. Jan Dahmen and co-workers (Jan Dahmen, et al., Carbohydr. Res. 111 C1-C4 (1982)) used bromoethyl group as the spacer arm which was later used to increase the length of the spacer arm with the desired functional groups such as: —CHO; —CO—N3; —CO—OOMe; —SH; etc. in order to allow for conjugation with the macromolecules. Lemieux, et al., (Can. J. Biochem. 55, 507-512 (1977) have used to a great extent 8-methoxycarbonyl octyl chain as a spacer arm, which at a later stage is converted into acylazide through multistep chemical sequences and then conjugated to the protein.

In the method proposed by Dahmen, et al., a hetero atom such as sulphur is introduced in the form of sulfide bond within the linking arm structure which in turn may exert a different effect on the production of antibodies. In view of these problems, we designed a spacer arm which would provide a quick and simple way of conjugation to the protein carrier.

Bernstein, et al., (Carbohydr. Res. 78:C1-C3 (1980) showed that if one designed a spacer arm having an isolated double terminal bond it is possible to obtain a chain which can be quickly converted into the very reactive aldehyde group by ozonolysis. The resultant compound can subsequently be conjugated to the protein carrier under mild reaction conditions. With these points in mind, 3,4,6-tri-O-acetyl-2-azido-2-deoxy-alpha-D-galactopyranosyl chloride has been glycosylated with 9-decen-1-ol under normal Koenigs-Knorr conditions. This reaction provided a mixture of alpha, beta mixtures of 9-decenyl-3,4,6-tri-O-acetyl-2-azido-2-deoxy-D-galactopyranosides. This alpha, beta-isomeric mixture was separated from the reaction residue, and was deacetylated using catalytic amount of sodium methoxide in methanol to provide an alpha, beta-isomeric mixture of 9-decenyl-2-azido-2-deoxy-D-galactopyranosides. A small portion of this mixture was used to separate the alpha, beta-isomers, namely 9-decenyl-2-azido-2-deoxy-alpha-D-galactopyranoside and 9-decenyl-2-azido-2-deoxy-beta-D-galactopyranoside and these isomers were characterized by $^1$H NMR. The remaining mixture was subjected to H$_2$S reduction (Adachi, et al., Synthesis 45 (1971)), followed by O-acetylation and N-acetylation to give alpha, beta-isomers of 9-decenyl-3,4,6-tri-O-acetyl-2-acetamido-2-deoxy-galactoyranosides. These alpha, beta isomers were separated at this stage using silica gel chromatography. The beta isomer was deacetylated using NaOMe/MeOH to give 9-decenyl-2-acetamido-2-deoxy-beta-D-galactopyranoside. This benzylidene derivative on glycosidation with 2,3,4,6-tetra-O-acetyl-alpha-D-galactopyranosyl bromide under Koenigs-Knorr conditions gave the appropriate disaccharide residue. This disaccharide on deprotection gave the deblocked form of 9-decenyl-3-O-(beta-D-galactopyranosyl)-2-acetamido-2-deoxy-beta-D-galactoopyranoise (12).

Ozonolysis reactions were performed on 9-decenyl-2-acetamido-2-deoxy-alpha-D-galactopyranoside and 9-decenyl-2-acetamido-2-deoxy-beta-D-galactopyranoside to investigate any changes in the nature of the production after ozonolysis. This experiment showed that ozonolysis did not affect the sugar moiety. Consequently we are confident that no alteration in sugar configuration occurs during the conjugation process to the carrier protein.

The synthon 3,4,6-tri-O-benzyl-2-azido-2-deoxy-alpha-D-galactopyranosyl chloride has the following advantages:

1. The presence of benzyl group as the protecting group provides a proper configuration for the addition of N$_3$. radical generated by a chemical method followed by the addition of a chloride ion supplied by one of the reagents used in the reaction processes. The effect of benzyl group has been illustrated by Bovin, et al., (Ref: J. Carbohydr. Chem. 2 (3) 249-262 (1983). This research group has done a comparative study on the reactivity of 3,4,6-tri-O-acetyl-D-galactal, 3,4,6-tri-O-benzyl-D-galactal and they showed with theoretical calculations and by experiments that the 3,4,6-tri-O-benzyl-D-galactal reacts 20 times faster than tri-O-acetyl-D-galactal, with good yield.

2. The presence of benzyl group will reduce considerably the number of steps involved in the synthesis of antigens like T-alpha and Tn having amino acids at the anomeric carbon. The actual steps involved are listed below.

(i) Glycosidation
(ii) Reduction—This single reaction will serve three purposes if benzyl group is used as a protecting group; (a) reduces N$_3$->NH$_2$; (b) deprotects the protecting groups on serine molecule; (c) removes the benzyl groups.

3. Acetylation of amino groups.

This method could avoid the racemization problem at the serine moiety which is a critical situation in this type of antigen synthesis.

EXAMPLE I

Synthesis of 3,4,6-tri-O-acetyl-2-azido-2-deoxy-alpha-D-galactopyranosyl Chloride (2)

A three neck flask (2 liter) was fixed with a mechanical stirrer (Kyrides seal), 400 mL dropping funnel and a 24-joint stopper. The three neck flask was placed in a cooling bath. It was flushed with oxygen-free nitrogen gas. 700 mL of acetonitrile (anhydrous) was added into the flask followed by the addition of 170.6 grams of $FeCl_3.6H_2O$ (0.1579×4 moles). The mixture was stirred until it became homogenous and brown in color. The mixture was cooled to between $-15°$ C. to $-20°$ C. After proper cooling, 13 grams (0.2 mole) of $NaN_3$ was added in batches. The solution became dark brown in color. Then 91.2 g (4 eq) of ammonium peroxydisulfate was added in one batch and the mixture was stirred vigorously. 3,4,6-tri-O-acetyl-D-galactal (1) (80% pure) (42.5 g) was dissolved in 250 mL of anhydrous acetonitrile and taken in the 500 mL dropping funnel A mixture of 8.6 g of $FeSO_4.7H_2O$, 50 mL acetonitrile, 1 mL $H_2O_2$ was prepared and without any delay, this mixture was added to the reaction system. Then the galactal solution was added drop-by-drop over a period of 40 minutes. During this addition the temperature was maintained at $-10°$ C.

After the complete addition of the galactal solution, another batch of 8.6 g of $FeSO_4.7H_2O$ (solid) and 1 mL $H_2O_2$ (30%) were added and the reaction mixture was stirred for another 7 hours at $-10°$ C. Then another batch of $NaN_3$ (113 g), $(NH_4)_2S_2O_8$ (2 eq), $FeCl_3.6H_2O$ (1 eq) and, $FeSO_4.7H_2O$ (0.03 moles) was added. After this addition the reaction mixture was gradually allowed to reach room temperature and stirred for another 17 hours. The reaction was followed by thin layer chromatography on silica gel coated glass plates using an ethylacetate-hexane (3:7) solvent system. After 24 hours in total, the stirring was stopped and the contents were allowed to settle. The inorganic solid was filtered and the filtrate was collected in a 2 liter flask. The solid material was washed in ether (50 mL×2). The filtrate was concentrated under rotary water pump vacuum at 25° C. until the volume was reduced to about 300 mL. Then the residue was taken in a 2 liter separatory funnel and 700 mL of ether was added. The ether solution was then washed with ice-cold water (300 mL×4). The ether solution was dried over anhydr. $Na_2SO_4$, filtered, and concentrated under vacuum at 25° C.

A silica gel column was prepared as follows. A glass column of 48 cm height and 60 cm diameter was packed with a slurry of flash silica gel (230-400 mesh) under moderate pressure to a height of 35 cm. The reaction residue was dissolved in 50 ml $CH_2Cl_2$ and the column was loaded with that solution. Then 500 mL of hexane was pumped at a flow rate of mL/min. This procedure was followed by the addition of an ethylacetate:hexane (3:7) mixture at a flow rate of 1 mL/min and 10 mL fractions were collected. The fractions having the rf value 0.59 in ethylacetate:hexane (4:6) solvent system were collected, concentrated and crystallized from etherhexane solvent mixture. The yield was 12 g of recrystallized product.

Compound 2 was characterized as follows:
$^1H$ NMR ($CDCl_3$): delta 6.24 (d,1H, 4 Hz, H-1), 5.56 (q, 1H, 1.5 Hz, H-4), 5.40 (q, 1H, 3.0 Hz, H-3), 2.20, 2.12, 2.10, (s, 9H, CO—$CH_3$)
m.p.: 85°-87° C.
$[alpha]D^{25}$: +143° (Cl, $CHCl_3$)

EXAMPLE II

Synthesis of 3,6-Di-O-acetyl-4-O-(2,3,4,6-tetra-O-acetyl-Beta-D-galactopyranosyl)-2-azido-2-deoxy-alpha-D-glucopyranosyl Chloride (4)

The title compound was obtained in a similar way as used for the synthesis of 3,4,6-tri-O-acetyl-2-azido-2-deoxyalpha-D-galactopyranosyl chloride (2).

To a solution of $FeCl_3.7H_2O$ (7.4 g) in 100 mL dry acetonitrile, ammonium peroxydisulphate (5.7 g), sodium azide (0.4 g) and ferrous sulphate (6.95 g) were added and the mixture was stirred at 0°-5° C. The hexaacetyl lactal (3) (2.8 g) in 20 mL dry acetonitrile was added over a period of 30 minutes to the reaction mixture was filtered, diluted with methylene chloride (200 mL), washed with sodium bicarbonate solution (100 mL) and cold water (100 mL), dried over anhydrous $Na_2SO_4$, filtered and concentrated to give an syrupy residue. This was fractioned over a column of silica gel and on elution with the solvent system used for thin layer chromatography analysis, yielded the required compound (0.8 g) as a solid.

Compound 4 was characterized as follows:
$[alpha]D^{25}$: +62.9° (C=1.1 CHCl3).
$^1HNMR(CDCl_3)$: delta 6.15 (d, 1H, 4.5 Hz, H-1); 4.55 (d, 1H, 7.00 Hz, H-1'); 3.90 (dd, 1H, 10.5 Hz, H-4); 3.75 (dd, 1H, 10.5 Hz, H-2); 2.00, 2.08, 2.10, 2.16, 2.18, 2.20 (S, 18 H, CO—$CH_3$)
m.p.: 138°-140° C.

EXAMPLE III

(a) Preparation of 9-decenyl-2-acetamido-2-deoxy-beta-D-galactopyranoside (9) and 9-decenyl-2-acetamido -2-deoxy-alpha-D-calactopyranoside (13)

9-Decenyl alcohol (4.68 g) was dissolved in 150 mL of 1:1 mixture of nitromethane and toluene. Mercuric cyanide (3.88 g) and mercuric chloride (5.42 g) and 40 g of drierite were added to the solution and the solution was concentrated by distillation at normal pressure until 30 mL of the solvent was collected. The reaction mixture was then cooled to 55° C. and 20 mL solution of 3,4,6-tri-O-acetyl-2-azido-2-deoxy-alpha-D-galactopyranosyl chloride (2) (5.23 g) in benzene was added over a period of 1 hour. The reaction mixture was heated for 72 hours under anhydrous nitrogen atmosphere. The reaction was then cooled to room temperature and filtered through a bed of celite. The filtrate was then extracted with $CH_2Cl_2$ (100 mL×4), washed with saturated solution of sodium bicarbonate (950 mL×2), 10% solution of KI (100 mL) and ice-cold water (100 mL); it was then dried over anhydrous sodium sulphate and concentrated under vacuum to give a syrupy residue (4 g) of compound 5. A portion of this residue (3.8 g) was dissolved in 100 mL anhydrous methanol and treated with 5 mL of 0.01 M solution of sodium methoxide and stirred at room temperature overnight. Afterwards the reaction mixture was neutralized with amberlite IR-120 (H+) resin and filtered. The filtrate was concentrated under vacuum to a residue which was washed with n-pentane to remove excess 9-decenol, leaving a solid compound 6 (2.5 g). This solid material was dissolved in 40 mL of pyridine and 40 mL of triethylamine. Then a slow stream of H$_2$S was passed at room temperature until a TLC analysis showed the disappearance of the starting material. The reaction was completed at 12 hours. Then the reaction mixture was concentrated at 35° C. under vacuum, co-evaporated with toluene several times, and finally dried completely using high vacuum. The resultant residue was then treated with acetic anhydride (30 mL) and pyridine (25 mL) and the reaction mixture was stirred at room temperature for 12 hours. Afterwards it was concentrated and extracted with dichloromethane (100 mL×3), washed with a saturated solution of sodium bicarbonate and extracted with dichloromethane (100 mL×3), dried over anhydrous Na$_2$SO$_4$, filtered and concentrated to give a crude product 7 (3.2 g).

This was subjected to a column chromatography over silica gel and eluted with ethylacetate:hexane:methanol (6.5:3.5:0.5) giving 9-decenyl-3,4,6-tri-O-acetyl-2-acetamido-2-deoxy-beta-D-galactopyranoside (8) (1.8 g) and 9-decenyl-3,4,6-tri-O-acetyl-2-acetamido-2-deoxy-alpha-D-galactopyranoside (8a) (1.3 g). The beta-isomer on deacetylation with catalytic amount of NaOMe in methanol followed by neutralization with Amberlite-120H+ resin provided 9 -decenyl-2-acetamido-2 -deoxy-beta-D-galactopyranoside (9) (1.0 g) which was recrystallized from methanol-water solvent mixture.

The beta isomer (compound 9) was characterized as follows:

$^1$H NMR (CD$_3$OD): delta (5.85m, 1H, CH═CH$_2$); 4.40 (d, 1H, 8.5 Hz, H-1), 2.02 (S, 3H, NH—CO—CH$_3$); 1.20–1.60 (m, CH$_2$-spacer arm).

m.p.: 203°–205° C.
[alpha]D$^{25}$=9.2° (C=1.0, CH$_3$OH)

The alpha-isomer was also characterized:
$^1$H NMR (CD$_3$OD): 5.82 (m, 1H, —CH═CH$_2$); 4.84(d, 1H, 4.4 Hz, H-1); 2.00 (S, 3H, —NH—CO—CH$_3$); 1.20–1.65(m, —CH$_2$-spacer arm).

m.p.: 174°–175° C.
[alpha]D$^{25}$: +136° (1.1CH$_3$OH)

EXAMPLE IV

Preparation of
9-Decenyl-2-acetamido-4,6-O-benzylidene-2-deoxy-beta-D-galactopyranoside (10)

9-Decenyl-2-acetamido-2-deoxy-beta-D-galactopyranoside (9) (0.900 g) was dissolved in 25 mL of N,N-dimethylformamide. A catalytic amount of p-toluene sulfonic acid (50 mg) was added to the above solution and the reaction mixture was heated for 12 hours at 60° C. The reaction was monitored by thin layer chromatography and upon completion, 1 mL of triethylamine was added and the reaction mixture was concentrated under vacuum at 35° C., diluted with 300 mL CH$_2$Cl$_2$, washed with water (100 mL), dried and concentrated to give the benzylidene derivative (10) (1.3 g).

$^1$H NMR (CDCl$_3$): delta 7.5 (m, 5H, —Ph); 6.00 (d, 1H, 6.20 Hz, —NH); 5.85 (m, 1H, —CH═CH$_2$); 5.60 (s, 1H, Ph—CH<); 4.70 (d, 1H, 7.80 Hz, H-1); 2.05 (s, 3H, NH—CO—CH$_3$); 1.60 (m, CH$_2$-Spacer arm).

EXAMPLE V

9-Decenyl-2-acetamido-3-O-(2,3,4,6-tetra-O-acetyl-beta-D-galactopyranosyl)-4,6-O-benzylidene-2-deoxy-beta-D-galactopyranoside (11)

9-Decenyl-2-acetamido-4,6-O-benzylidene-2-deoxy-beta-D-galactopyranoside (10) (1.2 g) was dissolved in a benzenenitromethane mixture (1:1, 50 mL), heated with mercuric cyanide (1.2 g) and 10 g of drierite, followed by distillation of 10 mL of the solvent. The mixture was then cooled to 60° C. and a solution of 2,3,4,6-tetra-O-acetyl-alpha-D-galactopyranosyl bromide (2.5 g) in 10 mL dry benzene was added and stirred at 60° C. for 12 hours. After the completion of the reaction, the reaction mixture was cooled to room temperature and filtered. The filtrate was extracted with dichloromethane (100 mL×3), washed with saturated sodium bicarbonate solution (100 mL×2), 10% KI solution (100 mL), water (100 mL×2) and finally dried and concentrated to give a foamy residue which was applied to a column of silica gel. The main fraction eluted with a hexane:ethylacetate:methanol (10:10:1) solvent mixture, after concentration, provided 9-decenyl-2-acetamido-3-O-(2,3,4,6-tetra-O-acetyl-beta-D-galactopyranosyl)-4, 6-O-benzylidene-2-deoxy-beta-D-galactopyranoside (11) (1.5 g).

Compound 11 was characterized:
$^1$H NMR (CDCl$_3$: delta 7.50 (m, 5H, —Ph); 5.90 (d, 1H, 7.0 Hz, —NH); 5.80 (m, 1H, —CH═CH$_2$); 5.60 (s, 1H, Ph—CH<); 5.20 (d, 1H, 7.60 Hz, H-1'); 4.80 (1H, d, 7.80 Hz, H-1); 2.20, 2.10, 2.02, 2.00 (s, 12H, —CO—CH$_3$, —NHCOCH$_3$); 1.50 (m, CH$_2$-spacer arm).

EXAMPLE VI

9-Decenyl-2-acetamido-2 -deoxy-3-O-(beta-D-galactopyranosyl)-beta-D-galactopyranoside (12)

9-Decenyl-2-acetamido-3-O-(2,3,4,6-tetra-O-acetyl-beta-D-galactopyranosyl)-4,6-O-benzylidene-2-deoxy-beta-D-galactopyranoside (11) (1.3 g) was O-deacetylated with a catalytic amount of sodium methoxide (5 mL 0.01M solution in methanol) in 50 mL of anhydrous methanol. The reaction mixture was neutralized with Amberlite IR-120 (H+) resin, filtered and concentrated to give a foam which was dissolved in 50 mL dichloromethane and treated with 1 mL of 90% aqueous trifluoroacetic acid and stirred for 5 minutes. Then the reaction mixture was de-ionized with Amberlite IRA-400 (OH$^-$), filtered, diluted with toluene and concentrated at 30° C. under vacuum to give 0.5 g of a solid which was homogeneous on thin layer chromatography. This solid was recrystallized from hot water (0.5 g) m.p. 206°–208° C. It was further characterized as follows:

[alpha]D$^{25}$=21.75° (C1.1 methanol)
$^1$H NMR (CD$_3$OD): delta 5.8(m, 1H, CH═CH$_2$), 4.5(d, 1H, 8.16 Hz, H-1), 4.32(d, 1H, 7.56 Hz, H-1), 1.94(s, 1H, —NH—), 2.1 (m, CH$_2$-spacer), 1.55(m, CH$_2$-spacer, 1.3 (m, CH$_2$-spacer).

EXAMPLE VII

Preparation of 1,3,4,6-tetra-O-acetyl-2-azido-2-deoxy-alpha-D-galactopyranose (14)

3,4,6- Tri-O-acetyl-azido-2-deoxy-alpha-D-galactopyranosyl chloride (2) (2 g) was treated with 50 mL glacial acetic acid and 5 g of mercuric acetate and the reaction mixture was stored at room temperature overnight. The reaction was followed by thin layer chromatography and after completion of the reaction, the mixture was diluted with dichloromethane (500 mL), washed with water (100 mL×4), sodium bicarbonate (100 mL×3), 10% KI solution (100 mL×1) and water (100 mL), dried (anhyd. $Na_2SO_4$) and evaporated. The residue (1.9 g) was dissolved in ether and allowed to cool to obtain pure crystalline alpha-isomer (0.800 g):

$^1$HNMR ($CDCl_3$): delta 6.38 (d, 1H, 3.9 Hz, H-1); 5.52 (d, 1H, 2.74, H-4), 5.36 (q, 1H, 10.96 Hz, H-3); 4.34 (m, 1H, H-5); 4.14 (m, 2H, H-6, H-6'); 3.95 (q, 1H, 10.9 Hz, H-2); 2.20, 2.10, 2.04 (s, 9H, —CO—$CH_3$).

M.P.: 113°-115° C.

[alpha]$D^{25}$: =90.00° (Cl, $CHCl_3$)

EXAMPLE VIII

Preparation of 3,4,6-Tri-O-acetyl-2-azido-2-deoxy-alpha-D-galactopyranosyl bromide (18)

1,3,4,6- Tetra-O-acetyl-2-azido-2-deoxy-alpha-D-galactopyranose (14) (500 mg) was dissolved in 50 mL $CH_2Cl_2$ (anhydrous), treated with 50 mL of $CH_2Cl_2$ saturated with HBr at 0° C., and stirred for two hours. Then 2 g of tetraethyl ammonium bromide was added and stirred overnight. Next, the solution was washed with 100 mL ice-cold water and concentrated. The residue was crystallized from ethyl ether and pentane to give 400 mg of 3,4,6-tri-O-acetyl-2-azido-2-deoxy-alpha-D-galactopyranosyl bromide (18).

$^1$H NMR ($CDCl_3$): delta 6.47 (d, 1H, 4.0 Hz, H-1): 5.49 (q, 1H, 2.7 Hz, H-4); 5.33 (q, 1H, 3.25, H-3); 4.48 (m, 1H, H-5); 3.96 (q, 1H, 10.5 Hz, H-2); 2.14, 2.04, 2.02 (3s, 9H, $CH_3$).

m.p.: 97°-99° C.

[alpha]$D^{25}$: +183° (Cl, $CHCl_3$)

EXAMPLE IX

Synthesis of 3,4,6-Tri-O-Benzyl-2-Azido-2-Deoxy-Alpha-D-Galactopyranosyl Chloride (20) and Alpha, Beta-Isomers of 3,4,6-Tri-O-Benzyl-2-Azido-2-Deoxy-2-Deoxy-D-Galactopyranose (21)

A solution of 3,4,6-tri-o-benzyl-D-galactal (19) (1.04 g) in dry acetonitrile (200 mL) cooled to −5° C. under inert atmosphere was added slowly over a period of 20 minutes to a mixture of 1.3 g of $FeCl_3.6H_2O$, 1.3 g of $FeSO_4.7H_2O$, 2.28 g of ammonium peroxydisulfate, 0.3 g of sodium azide, 0.2 mL of 50% hydrogen peroxide and 2.6 g of lithium chloride. The resulting reaction was followed by t.l.c. using ethyl acetate:hexane system (1:5). This was monitored by the disappearance of the starting material and the appearance of a new spot (Ref. value 0.61).

After the completion of the reaction, the reaction mixture was filtered through a filter paper, and the filtrate was concentrated. The residue was taken in 300 mL ether. The organic layer was washed with ice-cold water (100 mL×3), dried over sodium sulfate, filtered and evaporated to give a syrup (3.0 g) which was chromatographed over flash silica gel with ethyl acetate:hexane (4:6) as eluent. 3,4,6-tri-O-benzyl-2-azido-2-deoxy-alpha-D-galactopyranosyl chloride (20) was separated in 20% yield and the second compound, alpha, beta-isomers of 3,4,6-tri-o-benzyl-2-azido-2-deoxy-D-galactopyranose (21) in 40% yield.

Compound 20 was characterized as follows:

$^1$H NMR ($CDCl_3$) delta 6.20(d, 1H, 3.5 Hz H-1); 4.88 (d, 1H, 12 Hz, H—CH—$C_6H_5$); 4.76 (d, 2H, 2.5 Hz, $CH_2$—$C_6H_5$); 4.52 (d, 1H, 12 Hz, H—CH—$C_6H_5$); 4.48 (d, 2h, 12 Hz, CH—$C_6H_5$); 4.24 (m, 2H, H-2 and H-5); 4.10 (broad singlet, 1H, H-4); 4.00 (dd, 1H, J3, 4=3 Hz, H-3); 3.60 (m, 2H, H-6).

$^{13}$C NMR ($CDCl_3$) ppm: 94.5872 (C-1), 77.75 (C-5), 73.045, 72.7750 (C-4 and C-3), 61.0048 (C-2), 75.1413, 73.6770, 72.5953 ($CH_2$—$C_6H_5$) 67.8970 (C-6).

m.p.: 85°-86° C. (crystallized from ether-hexane two times)

[alpha]$D^{25}$: +102° C. (C=1.38, $CHCl_3$)

Anal (Calc for $C_{27}H_{28}N_3ClO_4$): C, 65.72; H, 5.69; N, 8.52; Cl, 7.19.

Found: C, 65.24; H, 5.69; N, 7.79; Cl, 7.09.

Compound 21 was similarly characterized:

$^1$H NMR $CDCl_3$: 7.3 (m, 15H, aromatic protons); 5.3 (s, 1H); 4.9 (d, 1H, 12.00 Hz, H—CH—$C_6H_5$); 4.50 (dd, 2H, 12.00 Hz, $CH_2$—$C_6H_5$); 4.14 (t, 1H, 6.0 Hz); 3.9 (m), 3.40 (q, 1H, 6.0 Hz); 3.3 (dd, 1H, 3.0 Hz).

$^{13}$C-NMR ($CDCl_3$) ppm: 6.5598 (C-1 beta, lit 96.5); 92.4563 (C-1 alpha lit 92.3). Pavia, et al., Int. J. Peptide Protein Res., 22, 549 (1983).

m.p.: 71°-73° C. (Crystallized from hexane: ether mixture)

[alpha]$D^{25}$: +32.5° (C=1.18, $CHCl_3$)

Anal: (Calc for $C_{27}H_{29}O_5N_3$) C, 68.19; H, 6.14; N, 8.83.

Found: C, 67.99; H, 5.94; N, 7.93.

EXAMPLE X

Preparation of Benzyl-N-(benzyloxycarbonyl)-O-(3,4,6-tri-O-benzyl-2-azido-2-deoxy-alpha-D-galactopyranosyl)-L-serinate (15)

A solution of benzyl-N-(benzyloxycarbonyl)-L-serinate (3 eq), tetraethylammonium bromide eq), and powdered 4 A molecular sieves (3 g) in dry methylene chloride (30 mL) was stirred overnight at room temperature.

In the meantime, in another flask, oxalyl bromide (3 eq) in 5 mL of dry methylene chloride was added dropwise to an ice-cold solution of 3,4,6-tri-O-benzyl-2-azido-deoxy-alpha, beta-D-galactopyranose (21) and dry DMF (3 Eq). This reaction mixture was allowed to reach room temperature and stirred overnight. The reaction was followed by t.l.c. using ethylacetate: hexane (1:4) solvent system. After the completion of the reaction, 100 mL of $CH_2Cl_2$ was added and the methylene chloride solution was washed quickly with ice-cold water (50 mL×2), dried (anhyd. $Na_2SO_4$) and concentrated to 30 mL solution. Without further purification, the solution was added to the solution of serine derivative and tetraethylammonium bromide. This reaction mixture was stirred for five days at room temperature. After completion of the reaction, the reaction mixture was filtered, extracted with $CH_2Cl_2$ (100 mL), washed with water (50 mL×3), dried (anhydrous $Na_2SO_4$) and concentrated. The residue was subjected to flash chromatography (E. Merck flash silica gel 200-430 mesh) using methylene chloride:ether:hexane (1:1:1.5) solvent system. The compound at Rf value 0.646 was separated (120 mg) and characterized by $^1$HNMR and $^{13}$CNMR spectra.

$^1$H NMR (CdCl$_3$) delta 7.20-7.50 (m, 25H, aromatic protons), 6.04 (d, 1H, 9 Hz, NH) 5.10 (d, 1H, 4 Hz, H-1)

$^{13}$C NMR (CdCl$_3$) ppm: 9.8217(C-1), 77.1234(C-5), 73.4651, 70.3506 (C-3 and C-4), 9.8677(C-2), 54.9177(C alpha-ser.), 67.2066, 67.6264, 72.3577, 73.5866, 74.8436 (CH$_2$—C$_6$H$_5$), 68.7637(C-6), 69.9876 (C beta-ser.)

[alpha]D$^{25}$ = +58.55° (C=1.38, CHCl$_3$)

EXAMPLE XI

Preparation of Benzyl-N-(benzyloxycarbonyl)-O-(3,4,6-tri-O-benzyl-2-acetamido-2-deoxy-alpha-D-galactopyranosyl)-L-serinate (16)

A solution of benzyl-N-(benzyloxycarbonyl)-O-(3,4,6-tri-O-benzyl-2-azido-2-deoxy-alpha-D-galactopyranosyl)-L-serinate (15) (100 mg) in 10 mL dry ethanol was added to a solution of nickel chloride (4%) and boric acid (2%) in 20 mL dry ethanol followed by the addition of sodium borohydride (50 mg) in 5 mL ethanol. After 4 hours at room temperature, acetic anhydride (10 mL) was added and the reaction mixture was stirred overnight at room temperature. After the completion of the reaction, the reaction mixture was concentrated under vacuum and the residue was extracted with dichloromethane (100 mL), washed with water (50 mL×2), dried (anhyd. Na$_2$SO$_4$) and concentrated. The residue was flash chromatographed over flash silica gel using a hexane:ethylacetate: methanol (10:10:1) (RF value 0.23) solvent system to provide 65 mg. This solid was recrystallized from an ethylacetate: hexane solvent mix of the title compound which was characterized by $^1$H NMR and $^{13}$C NMR spectra.

$^1$H NMR (CDCl$_3$) delta 7.30 (m, 25H, aromatic protons), 5.86 (d, 1H, 9.00 Hz, —NH), 4.82 (d, 1H, 4 Hz, H-1).

$^{13}$C NMR (CDCl$_3$) in ppm: 170.0967 (benzyloxycarbonyl C=O) 169.7903 (CO—NH) 99.4663 (C-1-alpha), 77.1697 (C-5), 72.6272, 70.4693 (C-3 and C-4) 54.7825 (C alpha-ser.), 49.1120 (C-2) 23.3544 (—CO—CH$_3$), 67.2653, 67.4449, 71.6376, 73.5681, 74.4823 (CH$_2$—C$_6$H$_5$), 69.0312 (C-6).

m.p.: 137°-138° C.

[alpha]D$^{25}$ = +52.50 (C=1.37, CHCl$_3$)

EXAMPLE XII

Preparation of O-(2-acetamido-2-deoxy-alpha-D-galactopyranosyl)-L-serine: (17) (Tn):

Benzyl-N-(benzyloxycarbonyl)-O-(3,4,6-tri-O-benzyl-2-acetamido-2-deoxy-alpha-galactopyranosyl)-L-serinate (16) (60 mg) was dissolved in methanol: acetic acid (10.1) mixture (10 mL) and hydrogenated at atmospheric pressure in the presence of 10% palladium charcoal at room temperature. After the completion of the reaction, the reaction mixture was filtered and concentrated under vacuum. The residue was passed through a column of Bio-gel-P-2 to provide a white solid (20 mg) m.p. 186°-187° C. (lit 186°) which was further characterized by $^1$H NMR and $^{13}$C NMR.

[alpha]D$^{25}$ = 143.46 (c=1.0 water)(lit 144°)

$^1$H NMR (D$_2$O) delta 4.76(d, 1H, 4 Hz, H-1), 4.04 (dd, 1H, J1, 2=4 Hz, H-2), 3.94 (dd, 1H, 3 Hz, H-4) 3.70-3.80 (m, 5H), 3.54-3.66 (m, 2H), 1.88 (s, 3H, —CO—CH$_3$)

$^{13}$C NMR (D$_2$O) in ppm: 176.1183 (CO—NH), 172.9674 (CO—OH), 99.4961(C-1), 72.8982(C$_5$), 69.9026, 69.0330 (C-4 and C-3), 51.0912 (C-2), 23.5051 (NH—CO—CH$_3$) 62.7138(C-6), 68.1337 (C beta-serine), 56.0265 (C alpha-serine).

TABLE OF COMPOUNDS 1. 3,4,6-tri-O-acetyl-D-galactal
2. 3,4,6-O-acetyl-2-azido-2-deoxy-alpha-D-galactopyranosyl chloride
3. 3,6,2',3',4',6'-hexa-O-acetyl-D-lactal
4. 3,6-di-O-acetyl-4-O-(2,3,4,6-tetra-O-acetyl-beta-D-galactopyranosyl)-2-azido-2-deoxy-alpha-D-glucopyranosyl chloride
5. 9-Decenyl-3,4,6-tri-O-acetyl-2-azido-2-deoxy-alpha,-beta-D-galactopyranoside
6. 9-Decenyl-2-azido-2-deoxy-alpha,beta-D-galactopyranoside
7. 9-Decenyl-3,4,6-tri-O-acetyl-2-acetamido-2-deoxy-alpha,beta-D-galactopyranoside
8. 9-Decenyl-3,4,6-tri-O-acetyl-2-acetamido-2-deoxy-beta-D-galacto pyranoside
8a. 9-Decenyl-3,4,6-tri-O-acetyl-2-acetamido-2-deoxy-alpha-D-galactopyranoside
9. 9-decenyl-2-acetamido-2-deoxy-beta-D-galactopyranoside
10. 9-decenyl-2-acetamido-4,6-O-Benzylidene-2-deoxy-beta-D-galactopyranoside
11. 9-decenyl-2-acetamido-3-O-(2,3,4,6-tetra-O-acetyl-beta-D-galactopyranosyl)-4,6-O-benzylidene-2-deoxy-beta-D-galactopyranoside
12. 9-decenyl-2-acetamido-2-deoxy-3-O-(beta-D-galactopyranosyl)-beta-D-galactopyranoside
13. 9-decenyl-2-acetamido-2-deoxy-alpha-D-galactopyranoside
14. 1,3,4,6-tetra-O-acetyl-2-azido-2-deoxy-alpha-D-galactopyranose
15. benzyl-N-(benzyloxycarbonyl)-O-(3,4,6-tri-O-benzyl-2-azido-2-deoxy-alpha-D-galactopyranosyl)-L-serinate
16. benzyl-N-(benzyloxycarbonyl)-O-(3,4,6-tri-O-benzyl-2-acetamido-2-deoxy-alpha-D-galactopyranosyl)-L-serinate
17. O-(2-acetamido-2-deoxy-alpha-D-galactopyranosyl)-L-serine.
18. 3,4,6-tri-O-acetyl-2-azido-2-deoxy-alpha-D-galactopyranosyl bromide
19. 3,4,6-tri-O-benzyl-D-galactal
20. 3,4,6-tri-O-benzyl-2-azido-2-deoxy-alpha-D-galactopyranosyl chloride
21. 3,4,6-tri-O-benzyl-2-azido-2-deoxy-alpha, beta-D-galactopyranose.

| Table of Reactions | | |
|---|---|---|
| 1->2 | azidochlorination | (Example I) |
| 3->4 | azidochlorination | (Example II) |
| 2->5 | glycosylation | (Example III) |
| 5->6 | deacetylation | (Example III) |
| 8->9 | deacetylation | (Example III) |
| 8a->13 | deacetylation | (Example III) |
| 9->10 | benzylidene subs. | (Example IV) |
| 10->11 | glycosylation | (Example V) |
| 11->12 | debenzylidenation | (Example VI) |
| 2->14 | acetylation | (Example VII) |
| 14->18 | bromination | (Example VIII) |
| 19->20 | glycosylation | (Example X) |
| 19->21 | reduction & | (Example XI) |

-continued

| | Table of Reactions | |
|---|---|---|
| 21->15 | acetylation debenzylation | (Example XII) |
| 15->16 | azidochlorination | (Example IX) |
| 16->17 | azidohydroxylation | (Example IX) |

We claim:

1. A process for azidochlorinating a non-manno 2-deoxy hexosyl glycal element of a carbohydrate which comprises reacting the glycal with a peroxyldisulfate salt, a ferrous salt, and azide salt and a chloride salt under conditions favoring the in situ generation of an azide free radical, whereby an azide group is attached to the C-2 carbon of the glycal and a chloride group is attached to the C-1 carbon.

2. The process of claim 1 in which the glycal is a galactal.

3. The process of claim 1 in which the glycal is a glucal.

4. The process of claim 1 in which the glycal is 3,4,6-protected.

5. The process of claim 4 in which the glycal is —O—-acetyl protected.

6. The process of claim 4 in which the glycal is —O—benzyl protected.

7. The process of claim 1 wherein the peroxydisulfate salt is peroxydisulfate ammonium.

8. The process of claim 1 wherein the ferrous salt is a ferrous sulfate.

9. The process of claim 8 in which the ferrous sulfate is hydrated.

10. The process of claim 1 in which the azide salt is sodium azide.

11. The process of claim 1 in which the chloride salt includes ferric chloride.

12. The process of claim 11, in which the chloride salt further includes lithium chloride.

13. The process of claim 11 in which the ferric chloride is hydrated.

14. The process of claim 1 in which the rinse product is selected from the group consisting of:
   (a) 3,4,6-tri-O-benzyl-2-azido-2-deoxy-D-galactopyranosyl chloride;
   (b) 3,4,6-tri-O-acetyl-2-azido-2-deoxy-alpha-D-galactopyranosyl chloride; and
   (c) 3,4,6-tri-O-benzyl-2-azido-2-deoxy-alpha-D-galactopyranose.

15. A process of preparing a synthetic antigen comprising the terminal disaccharide of asialo-$GM_1$ conjugated through a spacer arm to an immunogenic macromolecular carrier, which comprises:
   (a) preparing a 3,4,6-tri-O-protected, 2-azido-2-deoxy-alpha-D-galactopyranosyl chloride by the method of claim 1;
   (b) reacting it with an alcohol comprising a spacer arm suitable for connecting the molecule to an immunogenic macromolecular carrier, thus forming a 2-azido-2-deoxy galactopyranoside derivative;
   (c) reducing the 2-azido-group to a 2-acetamido group;
   (d) glycosylating the galactopyranoside with a galactopyranosyl chloride so as to produce a disaccharide with a beta (1->3) glycosidic linkage;
   (e) deprotecting the disaccharide; and
   (f) coupling the disaccharide through said spacer arm to an immunogenic carrier to provide said synthetic antigen presenting the terminal disaccharide of asialo $GM_1$.

16. A process of preparing Tn-alpha-O-serine which comprises:
   (a) preparing a 3,4,6-tri-O-protected 2-azido-2-deoxy-alpha-D-alpha-galactopyranosyl chloride by the process of claim 1;
   (b) hydrolyzing the product of step (a) to obtain a 3,4,6-tri-O-protected-2-azido-2-deoxy-alpha-D-galactopyranose;
   (c) reacting the product of step (b) with a protected O-serine;
   (d) reducing the 2-azido group to a 2-acetamido group; and
   (e) deprotecting the product of step(d) to obtain O-(2-acetamido-2-deoxy-alpha-D-galactopyranosyl)-L-serine.

17. The process of claim 15 in which the product of step (a) is O-acetyl protected.

18. The process of claim 16 in which the product of step (b) is O-benzyl protected.

19. A process for preparing a 1,2-diazide derivative of a glycal non-manno 2-deoxy hexosyl element of a carbohydrate which comprises reacting the glycal with a peroxydisulfate salt, ferric sulfate, a ferrous salt, and an azide salt under conditions favoring the in situ generation of an azide free radical.

20. The process of claim 19 in which the glycal is —O-benzyl protected.

21. A process for obtaining a carbohydrate comprising a 2-azido 2-deoxy hexosylbromide derivative of a glycal element in a non-manno configuration which comprises azidochlorinating such glycal element by the method of claim 1 to obtain an azidochloride derivative, hydrolyzing the azidochloride to obtain an azidohydroxide derivative, and brominating the azidohydroxide to obtain a carbohydrate comprising a 2-azido 2-deoxy hexosylbromide derivative of such glycal element.

22. The process of claim 1 wherein the glycal is reacted with ammonium peroxydisulfate, sodium azide, ferrous sulfate and ferric chloride.

23. The process of claim 22 in which 2 equivalents of ammonium peroxydisulfate, 4 equivalents of ferric chloride and 1 equivalent of sodium azide are reacted with glycal.

24. The process of claim 1 wherein the glycal element is selected from the group consisting of glucals, galactals and fucals.

25. The process of claim 19 wherein the glycal element is selected from the group consisting of glucals, galactals and fucals.

26. The process of claim 1 wherein the carbohydrate is a monosaccharide, disaccharide, trisaccharide or higher oligosaccharide.

27. The process of claim 24 wherein the carbohydrate is a monosaccharide, disaccharide, trisaccharide or higher oligosaccharide.

28. The process of claim 19 wherein the carbohydrate is a monosaccharide, disaccharide, trisaccharide or higher oligosaccharide.

29. The process of claim 25 wherein the carbohydrate is a monosaccharide, disaccharide, trisaccharide or higher oligosaccharide.

30. The process of claim 1 wherein the conditions favoring the in situ generation of an article free radical comprises providing hydrogen peroxide in an amount effective to act as a free radical reaction initiator.

31. The process of claim 1 wherein the carbohydrate comprises a lactal and an element of the lactal is azidochlorinated.

* * * * *